US00PP18255P2

(12) United States Plant Patent van Zoest B.V.

(10) Patent No.: US PP18,255 P2
(45) Date of Patent: Nov. 27, 2007

(54) *HYDRANGEA* PLANT NAMED 'ZORRO'

(50) Latin Name: *Hydrangea macrophylla*
Varietal Denomination: ZORRO

(76) Inventor: André van Zoest B.V., Randenburgseweg 25, Reeuwijk (NL), 2811 PS ( * ) Notice: Subject to any disclaimer, the term of this patent is extended or adjusted under 35 U.S.C. 154(b) by 0 days.

(21) Appl. No.: 11/282,382

(22) Filed: Nov. 18, 2005

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent Bell

(57) ABSTRACT

A new cultivar of *Hydrangea* plant named 'ZORRO' that is characterized by prominent dark purple-brown stems, dark green foliage and bright pink flowers. In combination these traits set 'ZORRO' apart from all other existing varieties of *Hydrangea* known to the inventor.

3 Drawing Sheets

Genus: *Hydrangea.*
Species: *macrophylla.*
Denomination: 'ZORRO'.

BACKGROUND OF THE INVENTION

The present invention relates to a new and distinct cultivar of *hydrangea* that is grown as an ornamental shrub for its prominent dark purple-brown stems, compact habit, dark green foliage and bright pink flowers. The new cultivar is known botanically as *Hydrangea macrophylla* and will be referred to hereinafter by the cultivar name 'ZORRO'.

'ZORRO' was discovered by the inventor at the inventor's nursery in Reeuwijk, The Netherlands in October 2000 as a whole plant which had developed from a naturally occurring branch mutation of the variety *Hydrangea macrophylla* 'Blaumeise' (unpatented). The unique characteristics of 'ZORRO' became apparent to the inventor when the original branch mutation matured into a whole plant.

'ZORRO' differs from the parent 'Blaumeise' in respect of plant habit and stem color. Whereas 'Blaumeise' achieves a height of 1.5 m after one year of production, 'ZORRO' only achieves a height of approximately 42.5 cm in one year. Whereas the stems of 'Blaumeise' are typically dark green as for the genus, the stems of 'ZORRO' are darker purple brown.

The closest comparison variety to 'ZORRO' known to the inventor is the dark stemmed variety *Hydrangea macrophylla* 'Nigra'. Whereas but *Hydrangea macrophylla* 'Nigra' is a mophead type of *Hydrangea,* 'ZORRO' is a lacecap type.

The distinguishing characteristic of 'ZORRO' is the very dark purple-brown coloration of the stems which are prominent in contrasting with the dark green foliage and bright pink flowers.

The first asexual reproduction of 'ZORRO' was conducted by the inventor in August 2001 in a cultivated area of Boskoop, The Netherlands. The method used for asexual propagation was softwood cuttings. The inventor has determined that the characteristics of the 'ZORRO' are fixed and are reproduced true to type in successive generations of asexual propagation.

An application for a grant of European Community Plant Breeders Rights was filed on Dec. 3, 2001, Serial number 2001/1943. This application has matured into a grant of European Community Plant Breeders Rights, issued on Jun. 21. 2004, grant number 13,555.

All plants of 'ZORRO' remained at the breeder's premises and under the breeder's control until the breeder made the first sale and delivery in March 2005.

SUMMARY OF THE INVENTION

The following traits have been repeatedly observed and represent the characteristics of the new *Hydrangea* cultivar 'ZORRO'. These traits in combination distinguish 'ZORRO' form all other commercial varieties known to the inventor. 'ZORRO' has not been tested under all possible conditions and phenotypic differences may be observed with variations in environmental, climatic and cultural conditions, without however, any difference in genotype.

1. *Hydrangea* 'ZORRO' is a dwarf shrub.
2. *Hydrangea* 'ZORRO' exhibits a compact, upright, inverted triangular habit.
3. *Hydrangea* 'ZORRO' exhibits dark green foliage.
4. *Hydrangea* 'ZORRO' exhibits dark purple brown stems.
5. *Hydrangea* 'ZORRO' is 42.5 cm. in height and 42.5 cm. in width at 1 year 6 months from rooting an initial cutting.
6. *Hydrangea* 'ZORRO' is hardy in USDA Zone 5.

BRIEF DESCRIPTION OF THE DRAWINGS

The accompanying three color drawings illustrate the overall appearance of the new cultivar 'ZORRO' showing the colors as true as it is reasonably possible to obtain in colored reproductions of this type. Colors in the photographs may differ from the color values cited in the detailed botanical description, which accurately describe the actual colors of the new variety of *Hydrangea* named 'ZORRO'.

The drawing labeled as FIG. 1 shows a side view of a single plant of 'ZORRO' with foliage, six inflorescences in various stages, and the characteristically dark stems. The plant in this drawing is 13 months old from rooting on an initial cutting and has been grown out of doors in The Netherlands. The plant has been grown in a peat-based growing medium of pH in the range 6.0 to 6.4.

Figure 1:
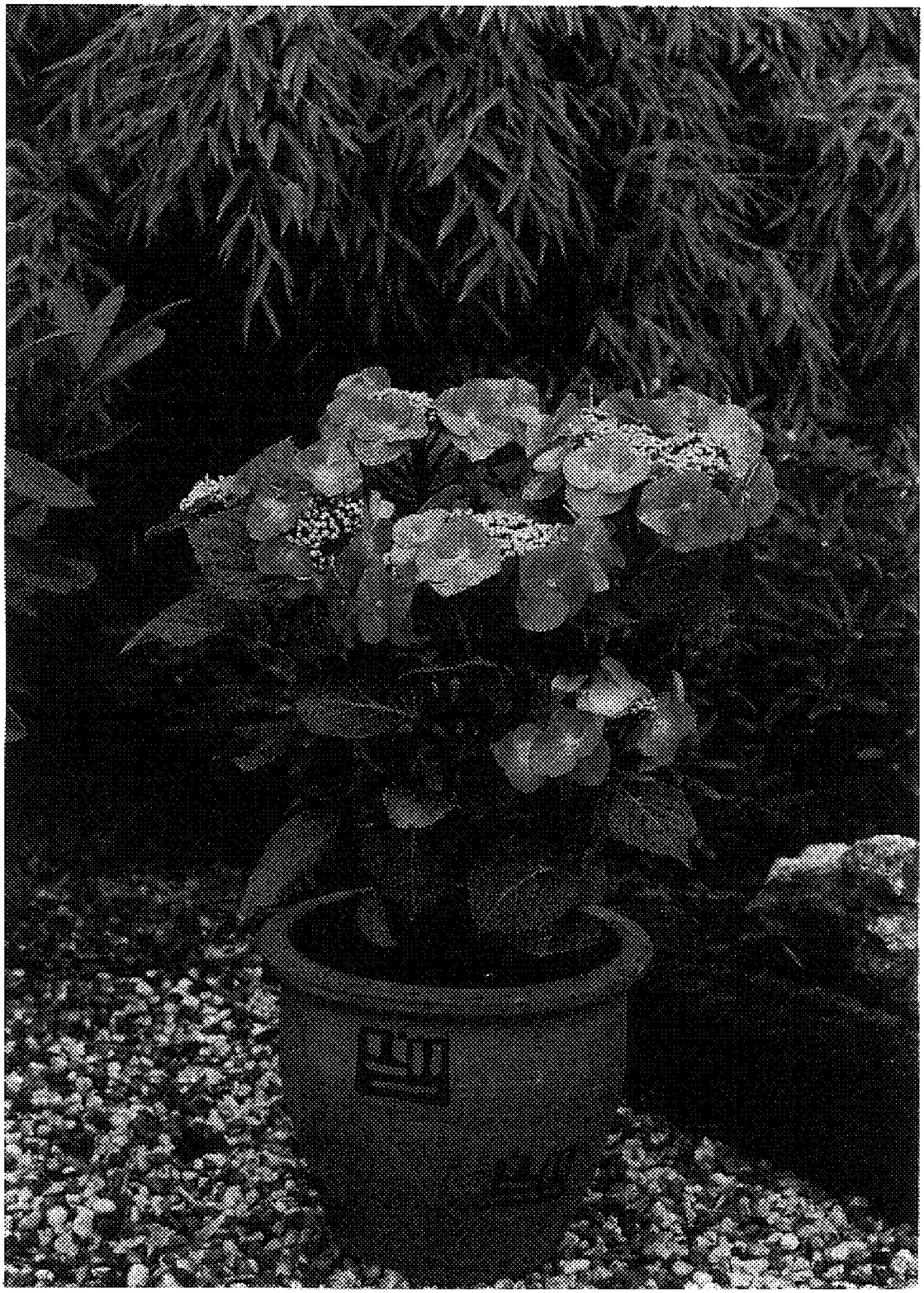
Figure 2:
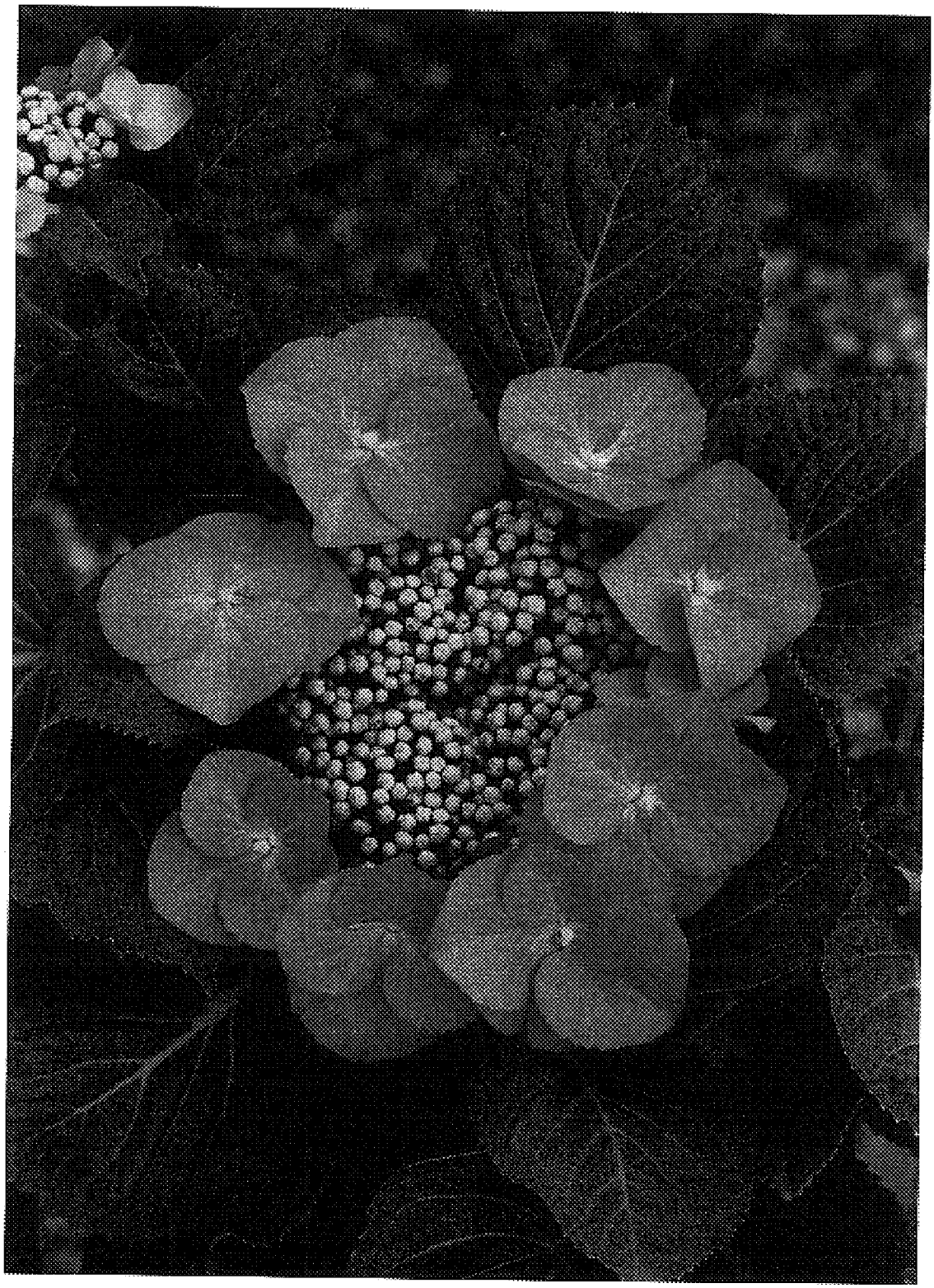

The drawing labeled as FIG. 2 is a close-up of a typical inflorescence showing sterile and fertile flowers.

Figure 3:
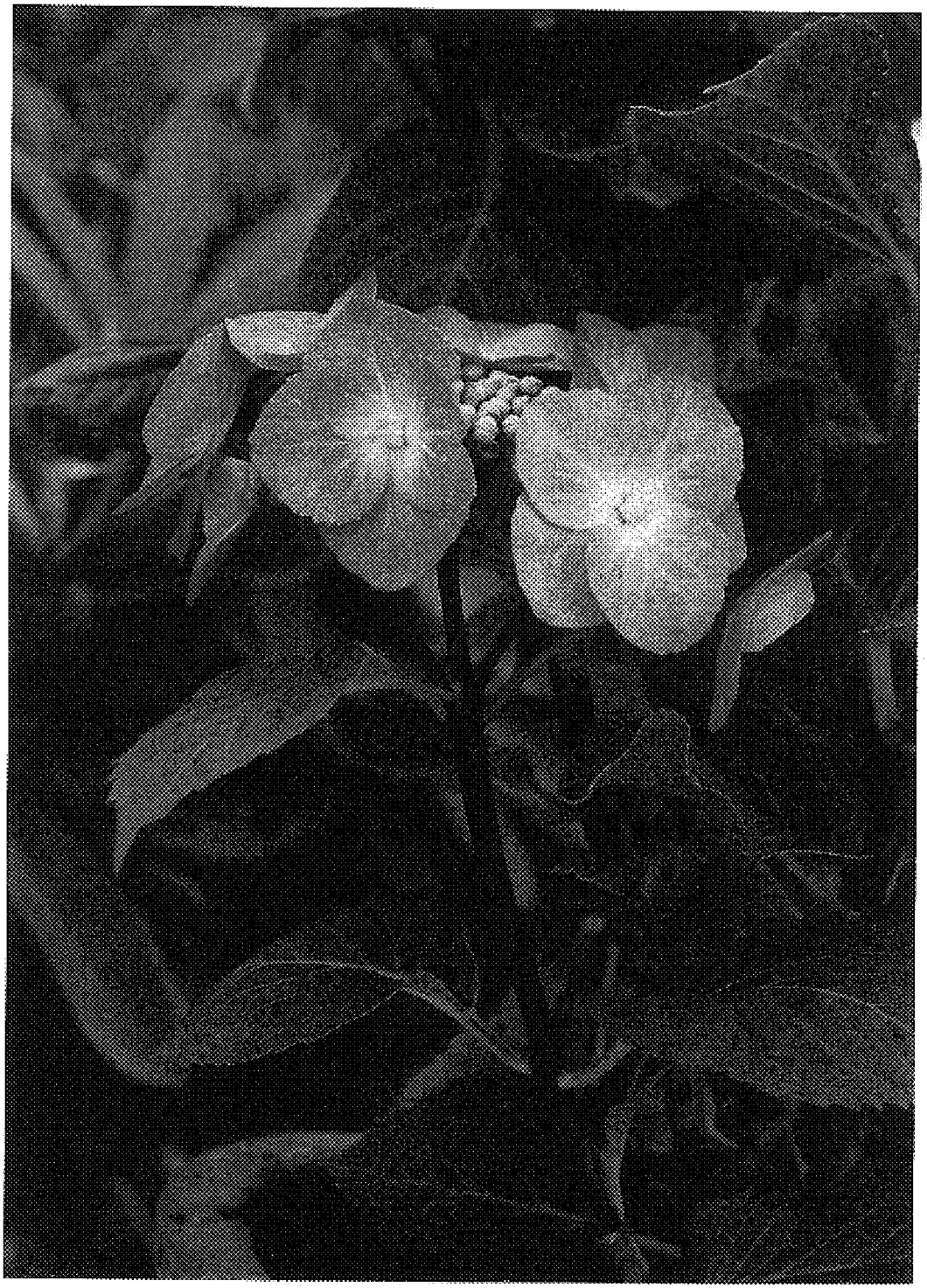

The drawing labeled as FIG. 3 presents a close-up view of the dark purple brown stems of 'ZORRO'.

All drawings were made using conventional techniques and although colors may appear different from actual colors due to light reflectance they are as accurate as possible by conventional photography.

BOTANICAL DESCRIPTION OF THE PLANT

The following is a detailed description of 'ZORRO' as grown under normal outdoor growing conditions in Boskoop, The Netherlands. Data was collected over time from a plant which was 12–15 months old from an initial cutting. The subject plant had been grown in a peat-based growing medium of pH in the range 6.0 to 6.4. The color determinations are in accordance with the 2001 edition of The Royal Horticultural Society Colour Chart except where general color terms of ordinary dictionary significance are used.

Botanical classification:
Genus: *Hydrangea.*
Species: *macrophylla.*
Denomination: 'ZORRO'.
Commercial classification: Deciduous shrub.
Common names: Big leaf *hydrangea.* Lace cap *hydrangea.*
Use: Plant in gardens and landscapes or in patio containers.
Container size: Suggested container size: 5-liter and above.
Cultural requirements: Plant in a peat based growing medium of pH in the range of 6.0 to 6.4.
Plant description:
- *Bloom period.*—Summer.
- *Commercial category.*—Deciduous shrub.
- *Plant habit.*—Compact, upright and spreading.
- *Dimensions.*—42.5 cm in height, 42.5 cm in width in an 18 months old plant.
- *Hardiness.*—USDA Zones 5.
- *Root system.*—Fibrous, moderately fleshy.
- *Propagation.*—Propagation is accomplished using softwood cuttings.
- *Time to develop roots.*—Average is 2 months.
- *Crop time.*—1 year to a 5 l container.

Stem:
- *Stem shape.*—Rounded.
- *Dimensions.*—28.3 cm in length, 8 mm in diameter.
- *Stem surface.*—Smooth, glossy.
- *Stem color.*—N186C.
- *Internode length.*—6.5 cm. between nodes.

Foliage:
- *Type.*—Deciduous.
- *Number leaves per stem.*—10 (5 pairs).
- *Arrangement.*—Opposite.
- *Leaf shape.*—Broad ovate.
- *Division.*—Simple.
- *Leaf dimensions.*—11 cm in length, 8.4 cm in width.
- *Apex.*—Abruptly acute.
- *Base.*—Broadly attenuate.
- *Leaf margins.*—Serrate.
- *Venation pattern.*—Pinnate.
- *Vein color* (*adaxial*).—145B.
- *Vein color* (*abaxial*).—145C.
- *Leaf surface* (*adaxial and abaxial*).—Smooth, dull.
- *Young leaf color* (*adaxial*).—143A.
- *Young leaf color* (*abaxial*).—143C.
- *Mature leaf color* (*adaxial*).—137A.
- *Mature leaf color* (*abaxial*).—137D.
- *Attachment.*—Petiolate.
- *Petiole color.*—144A and 144B with slight tinges of 184A and 184B.
- *Petiole surface.*—Smooth, slightly glossy.
- *Petiole dimensions.*—1.9 cm in length, 4 mm in diameter.
- *Fragrance.*—None observed.

Flowers:
- *Inflorescence type.*—Flattened compound corymb.
- *Inflorescence type.*—Compound corymb.

Quantify of flowers per inflorescence: An average of 185 fertile flowers, and 10 sterile flowers.
Flowering habit: Blooms during the summer.
Fertile flowers:
- *Bud shape.*—Flattened globular.
- *Bud color.*—145A and 145B.
- *Bud dimensions.*—4 mm in length and 5 mm in diameter.
- *Flower aspect.*—Facing upward and outward.
- *Flower shape.*—Rotate.
- *Flower dimensions.*—7 mm in diameter, 3 mm in depth.
- *Corolla dimensions.*—Average length 4 mm, average width 7 mm.
- *Shape of corolla tube.*—No corolla tube present.
- *Petals fused or unfused.*—Unfused.
- *Petal shape.*—Broad ovate, strongly concave.
- *Petal apex.*—Gently obtuse, almost rounded.
- *Petal margin.*—Entire towards apex and base, otherwise denticulate.
- *Petal base.*—Cordate.
- *Number of petals.*—Average of 5.
- *Petal color* (*adaxial surface*).—94C and 94D.
- *Petal color* (*abaxial surface*).—94D.
- *Petal surface* (*adaxial*).—Smooth, dull.
- *Petal surface* (*abaxial*).—Smooth, slightly glossy.
- *Peduncle shape.*—Rounded.
- *Peduncle dimensions.*—Average length 5.3 cm, average with 4 mm.
- *Peduncle color.*—N186C.
- *Peduncle surface.*—Slightly glossy.
- *Other peduncle structures.*—Sparsely covered with very short grey-white hairs, average length 0.2 mm.
- *Calyx shape.*—Campanulate.
- *Calyx dimensions.*—Average length 3 mm, average width 3.5 mm.
- *Calyx color* (*outer surface*).—144A.
- *Calyx color* (*inner surface*).—145A.
- *Calyx surface* (*outer*).—Smooth, slightly glossy.
- *Calyx surface* (*inner*).—Smooth.
- *Number of sepals.*—Average of 5.
- *Sepals fused or unfused.*—Base (lower 66%) fused.
- *Sepal color* (*adaxial surface*).—144A.
- *Sepal color* (*abaxial surface*).—145A.
- *Sepal surface* (*adaxial*).—Smooth, slightly glossy.
- *Sepal surface* (*abaxial*).—Smooth.

Sterile flowers:
- *Number of bracts per inflorescence.*—10.
- *Bracts fused or unfused.*—Unfused.
- *Bract shape.*—Cordate to deltoid.
- *Bract apex.*—Broad acute to rounded.

*Bract margin.*—Entire.
*Bract base.*—Truncate to cordate.
*Bract dimensions.*—Average length 2.2 cm, average width 2.5 cm.
*Bract color* (*adaxial surface*).—72B with some N88B; base 150C.
*Bract color* (*abaxial surface*).—84B, base 150C.
*Bract surface* (*adaxial and abaxial surfaces*).—Smooth, dull.

Reproductive organs (fertile flowers):
*Pistil.*—One thick pistil with a trifid stigma.
*Pistil shape.*—Ovate.
*Pistil dimensions.*—Average length 2.5 mm, average width 1.5 mm.
*Pistil color.*—145B.
*Pistil surface.*—Smooth, not very glossy.
*Stigma shape.*—Trifid.
*Stigma dimensions.*—Average length 1.5 mm, average width 2 mm.
*Stigma color.*—145B.
*Style shape.*—Ovate.
*Style dimensions.*—Average length 1 mm, average width 1.5 mm.
*Style color.*—145A and 145B.
*Number of stamens.*—On average 3 (strongly deformed).
*Fused or unfused.*—Unfused.
*Stamen dimensions.*—Average length 2 mm, average width 1 mm.
*Stamen color.*—144B.
*Anther shape.*—Club-shaped.
*Anther dimensions.*—Average length 0.5 mm, average width 0.4 mm.
*Anther color.*—144B.
*Pollen color and amount.*—No pollen observed.
*Ovary position.*—Inferior.
*Ovary shape.*—Ovate.
*Ovary dimensions.*—Average length 2 mm, average width 1.5 mm.
*Ovary color.*—144A.

Seed production: No seed production has been observed to date.

What is claimed is:

1. A new and distinct cultivar of *Hydrangea* plant named 'ZORRO' as described and illustrated herein.

* * * * *